(12) United States Patent
Serrano et al.

(10) Patent No.: US 8,148,425 B2
(45) Date of Patent: Apr. 3, 2012

(54) PHARMACEUTICAL COMPOSITION CONTAINING PHLOROGLUCINOL AND PARACETAMOL

(75) Inventors: Jean-Jacques Serrano, Montpellier (FR); Claudette Serrano, Montpellier (FR)

(73) Assignee: Promindus (Actions Promotionnelles Dans l'Industrie et le Commerce), Casablanca (MA)

( * ) Notice: Subject to any disclaimer, the term of this patent is extended or adjusted under 35 U.S.C. 154(b) by 57 days.

(21) Appl. No.: 12/527,592

(22) PCT Filed: Feb. 18, 2008

(86) PCT No.: PCT/FR2008/050263
§ 371 (c)(1),
(2), (4) Date: Jan. 20, 2010

(87) PCT Pub. No.: WO2008/113929
PCT Pub. Date: Sep. 25, 2008

(65) Prior Publication Data
US 2010/0168238 A1    Jul. 1, 2010

(30) Foreign Application Priority Data
Feb. 19, 2007   (FR) ...................................... 07 53351

(51) Int. Cl.
*A61K 31/195* (2006.01)
(52) U.S. Cl. ......... 514/563; 514/734; 424/466; 424/474
(58) Field of Classification Search .................. 514/563, 514/734; 424/466, 474
See application file for complete search history.

(56) References Cited

U.S. PATENT DOCUMENTS

| | | | | |
|---|---|---|---|---|
| 4,309,408 A | * | 1/1982 | Pathak et al. | 424/44 |
| 6,716,884 B1 | * | 4/2004 | Bennis et al. | 514/734 |
| 7,199,153 B2 | * | 4/2007 | Clarke et al. | 514/474 |

FOREIGN PATENT DOCUMENTS

WO    WO 97/19680    6/1997

OTHER PUBLICATIONS

Kambia et al. Eur. J. Hospital Pharm. Science, 2006, 12, 91-95.*
Author Unknown, "Liquid Preparations for Cutaneous Application", European Pharmacopeia, Jan. 2008, 728-730.
Author Unknown, "Mucoadhesive Preparations", European Pharmacopoeia 6.0, Jan. 2008, 735-737.
Casha et al., "Latrodectisme chez un enfant", Archives De Pediatrie, 1998, 5(5), 510-512, XP005260394.
Fournier-Charriere et al., Les Medicaments De La Douleur Chez L'Enfant, Press Medicale, 1997, 26(19), 925-932, XP001051488.
Kambia et al., "Stability and Compatibility of the Ready-to-use Solution of Paracetamol Admixed with Phloroglucinol for Intravenous Infusion", Eur. Journal Hospital Pharm Science, 2006, 12(5), May 2006, 91-95.
Lacroix et al., "Consommation de medicaments en Periode Perinatale: Etude Comparative chaz des femmes allaitant ou non leur enfant", J. Pediatrie Puericulture, 2005, 18(8), 379-385, XP005204519.

* cited by examiner

*Primary Examiner* — Jeffrey S. Lundgren
*Assistant Examiner* — Ibrahim D Bori
(74) *Attorney, Agent, or Firm* — Woodcock Washburn LLP

(57) ABSTRACT

The invention relates to a pharmaceutical composition for oral or rectal administration, that contains phloroglucinol and paracetamol in a pharmaceutically acceptable carrier. The inventors have evidenced a synergy developed by these two active ingredients in antispasmodic therapy.

13 Claims, No Drawings

PHARMACEUTICAL COMPOSITION CONTAINING PHLOROGLUCINOL AND PARACETAMOL

This application is the National Phase of International Patent Application No. PCT/FR2008/050263, filed Feb. 18, 2008, which claims the benefit of French Patent Application No. 0753351, filed Feb. 19, 2007, the entireties of which are incorporated herein.

The subject of the present invention is a pharmaceutical composition containing an antispasmodic (phloroglucinol) and an analgesic (paracetamol). Said composition, which is suitable for oral or rectal administration, is particularly effective in antispasmodic therapy.

A spasm is a sudden, intense, very painful involuntary contraction. It may be of renal origin in the case of nephritic colic, of hepatic origin in the case of hepatic colic, of intestinal origin in the case of intestinal spasms and of spastic colitis, or of gynecological origin in the case of dysmenorrhea. Irrespective of the origin thereof, the spasm is accompanied by extremely intense and persistent pain.

Two types of antispasmodic exist:
neurotropic antispasmodics, such as atropine and derivatives thereof, scopolamine, quaternary ammoniums such as tiemonium iodide, butylhyoscine bromide, etc., and
musculotropic antispasmodics, such as papaverine, mebeverine, trimebutine, pinaverium bromide, phloroglucinol and derivatives, etc.

The neurotropic antispasmodics are less commonly used due to adverse effects which follow from their antimuscarinic pharmacological action. In fact, muscarinic receptors are very widely distributed in a variety of organs and of peripheral and central tissues. Thus, a desired pharmacological action, on intestinal peristalsis for example, is in most cases accompanied by adverse effects on salivary secretion, the heart, the respiratory system, the urogenital system, etc. In addition, said neurotropic antispasmodics are strictly contraindicated in the case of glaucoma, prostatic hypertrophy, micturition disorders, pyloric stenosis, etc.

On the other hand, musculotropic antispasmodics, which are much better tolerated, with more limited secondary actions, are much more commonly used. Thus, phloroglucinol relaxes the contracted smooth fiber irrespective of the type of contraction, without other systemic effects, or any contraindication, even at high dose.

The following may be specified with reference to phloroglucinol (CAS: 108-73-6; 1,3,5-trihydroxy-benzene). It is very widely known and used, alone, as an active ingredient for medicaments. It is thus a musculotropic antispasmodic. It is particularly active on the digestive system and the urogenital system. It relieves the smooth muscle fiber spasm and as a result soothes the pain. It is particularly indicated for:
the symptomatic treatment of pain related to functional disorders of the gastrointestinal type and of the bile ducts;
the treatment of acute spasmodic and painful manifestations of the urinary tracts: nephritic colic;
the symptomatic treatment of painful spasmodic gynecological manifestations;
the adjuvant treatment of contractions during pregnancy in combination with rest.

Phloroglucinol is perfectly well-tolerated, and has no or negligible side effects: at the very most, it has been possible to note, very rarely, some skin reactions of allergic type. It is not teratogenic or mutagenic. Clinically, the very widespread use of phloroglucinol has revealed no risk of malformation to date. It is not known to have any contraindications or any particular precautions for use, except with morphine, which has a spasmogenic effect.

It is used in various forms, more particularly in the form of:
coated tablets,
lyophilizates (Lyocs),
effervescent tablets,
injectable solutions.

The toxicity of phloroglucinol is very weak. By way of example, it is possible to take up to eight Lyocs (lyophilized systems) per day (which represents 640 mg) or three injectable vials of 40 mg intravenously per day.

Phloroglucinol is also used in children.

Paracetamol (CAS: 103-90-2; 4-acetylaminophenol) is itself also very widely known and used as an active ingredient of medicaments. It is used alone or in combination with another active ingredient such as codeine or vitamin C. To the inventors' knowledge, it has not been combined with an antispasmodic. However, a publication—THE EUROPEAN JOURNAL OF HOSPITAL PHARMACY SCIENCE, Vol. 12, No. 5, 2006, pages 91-95—exists which presents the results of a physicochemical study of stability and compatibility of paracetamol and phloroglucinol, formulated together, in solutions for intravenous injection. This publication, which is strictly analytical, mentions only intravenous administration, contains no result of pharmacological tests, and neither describes nor suggests any potentiating synergy (see below).

Paracetamol is a compound which is particularly indicated as an analgesic and for its antipyretic properties. It is a substance that is perfectly well-tolerated in adults and in children. Of all the antipyretic analgesics, it is the most widely used. It has no anti-inflammatory properties and therefore does not develop any gastrotoxicity, even when taken chronically and at a high dose. It has no or negligible side effects: at the very most, it has been possible to note some rare cases of hypersensitivity, reversible upon interruption of the treatment.

Paracetamol is neither teratogenic nor mutagenic. On the other hand, at very high doses, corresponding to cases of very large overdoses (since it is necessary to reach doses of 10 g per day), it can trigger severe hepatic toxicity. This type of overdose is exceptional since paracetamol is used and is effective without having to exceed, in the most severe cases, the dose of 4 g per day.

Paracetamol is used in various forms, more particularly in the form of:
tablets, in particular effervescent tablets and orodispersible tablets,
pediatric oral solutions,
effervescent powders,
suppositories,
injectable solutes.

In such a context, the inventors propose combining said two known active ingredients:
on the one hand, phloroglucinol and
on the other hand, paracetamol.

The choice of paracetamol, among the existing analgesics, is particularly advantageous. Other analgesics have been judiciously set aside, such as:
nonsteroidal anti-inflammatories or derivatives thereof, known for their analgesic properties when they are used at low doses, but having, even at said low doses, the drawbacks of anti-inflammatories;
aspirin (acetylsalicylic acid) which is not only gastrotoxic, but also a platelet antiaggregant;

tramadol, which has a central action and is capable of causing a dependence phenomenon and a withdrawal syndrome;

dextropropoxyphene, an opioid analgesic.

Said phloroglucinol+paracetamol combination develops moreover, entirely surprisingly, in an antispasmodic therapy context, a synergy that potentiates the actions of each of said phloroglucinol and paracetamol. To obtain an equivalent effectiveness, in the context of the combination, less of at least one of said active ingredients is used.

It is to the inventors' credit to have demonstrated said synergy and therefore the great advantage of the combination: phloroglucinol+paracetamol.

The first subject of the present invention concerns a pharmaceutical composition, for oral or rectal administration, which comprises, on the one hand, phloroglucinol and, on the other hand, paracetamol, in a pharmaceutically acceptable excipient. Within said composition, the two active ingredients are formulated together (a unit form is in question); they are formulated together for oral or rectal administration. The pharmaceutically acceptable excipient is suitable for such an oral or rectal administration.

The pharmaceutical compositions of the invention contain the two active ingredients identified above. Advantageously, they contain no other active ingredient(s). However, the use of at least one other active ingredient in said pharmaceutical compositions could not in any way be excluded.

The pharmaceutically acceptable excipient is not, per se, original. It is suitable for the formulation of the two active ingredients. It is suitable for the desired route of administration (orally or rectally), for the nature of the desired galenic form.

The pharmaceutical compositions of the invention are available in any of the galenic forms suitable for oral or rectal administration. Said galenic forms may in particular comprise: tablets, capsules, powders, granules, lyophilizates, oral solutes, syrups, suspensions and suppositories.

This list is not exhaustive.

The term "tablet" denotes tablets of all types, and in particular effervescent tablets, dispersible tablets and orodispersible tablets.

According to the invention, the active ingredients in question—phloroglucinol and paracetamol—are advantageously formulated, together, in the form of effervescent tablets. Such effervescent tablets generally generate (aqueous) solutions of which the pH is between 3 and 7. They advantageously generate solutions of which the pH is in the region of or equal to 5.

The effervescent tablets in question develop the effervescence in a manner known per se, in particular by virtue of the combination in their formulation:

of at least one organic acid and/or of at least one salt of an organic acid; and of at least one strong base and/or of at least one salt of a strong base.

Said at least one organic acid is advantageously chosen from citric acid, tartaric acid, malic acid and acetic acid; said at least one salt of a strong base is advantageously chosen from sodium bicarbonate, sodium carbonate, calcium bicarbonate, calcium carbonate, magnesium bicarbonate, magnesium carbonate, potassium bicarbonate and potassium carbonate.

In the context of the present invention, effervescent tablets (containing the two active ingredients: phloroglucinol and paracetamol) are particularly preferred.

The pharmaceutical compositions of the invention contain generally from 50 to 200 mg of phloroglucinol. They contain in particular 80, 100 or 160 mg of phloroglucinol.

Similarly, they contain generally from 100 to 1000 mg of paracetamol, advantageously from 100 to 500 mg of paracetamol. According to one preferred variant, said compositions contain less than 500 mg of paracetamol, and in particular from 100 to less than 500 mg of paracetamol.

Those skilled in the art, in view of the potency of the action desired, are able to optimize the absolute and relative amounts, of the two active ingredients, involved. Given the potentiating synergy demonstrated, a smaller amount of active ingredients is used for an equivalent (but more rapid) effect, or, at an equivalent amount used, a more potent and more rapid action is observed.

The pharmaceutical compositions of the invention, recommended in antispasmodic therapy, are most particularly recommended in the treatment of spasmodic conditions, such as spastic colitis, hepatic colic, nephritic colic and dysmenorrhea.

According to another of its subjects, the present invention concerns the preparation of a pharmaceutical composition as described above. Said preparation characteristically comprises the formulation of phloroglucinol and paracetamol, together, in a pharmaceutically acceptable excipient suitable for oral or rectal administration.

The term "formulation" is familiar to those skilled in the art. The techniques for formulating the two active ingredients in question are not, per se, innovative. They essentially comprise mixing the two active ingredients with the appropriate excipient, with generally the various elements making up said excipient.

According to another of its aspects, the present invention concerns the use of phloroglucinol and of paracetamol for the preparation of a pharmaceutical composition, suitable for oral or rectal administration, for use in treating spasmodic conditions. Said pharmaceutical composition advantageously consists of a galenic form, as specified above, which advantageously contains the phloroglucinol and the paracetamol in the amounts indicated above.

The invention will now be illustrated hereinafter, in a manner that is in no way limiting.

EXAMPLES a) Effervescent tablets of the invention were prepared by combining, respectively, 80, 100 and 160 mg of phloroglucinol with 125, 250, 400, 500, 750 and 1000 mg of paracetamol, in a pharmaceutically acceptable excipient containing:

| | |
|---|---|
| citric acid | q.s. |
| sodium bicarbonate | q.s. |
| docusate sodium | q.s. |
| povidone | q.s. |
| sodium saccharin, and | q.s. |
| sodium benzoate | q.s. |

Such tablets generate solutions at a pH of 5.

The exact composition by mass of an effervescent tablet of this type is indicated below:

| | |
|---|---|
| Phloroglucinol | 80 mg |
| Paracetamol | 250 mg |

-continued

| | |
|---|---|
| Sodium bicarbonate | 295.2 mg |
| Citric acid | 215 mg |
| Povidone | 35 mg |
| Sodium benzoate | 15.2 mg |
| Docusate sodium | 0.2 mg |
| Sodium saccharin | 0.5 mg | b) Finally, it is proposed to illustrate the advantage of the present invention by presenting hereinafter comparative results of pharmacological tests.

During said tests, the antispasmodic and analgesic activity of phloroglucinol, of paracetamol, and of phloroglucinol combined with paracetamol was evaluated using the Siegmund test or "Writhing test". The principle of this test, which is familiar to those skilled in the art, is briefly summarized hereinafter. The intraperitoneal injection of phenylbenzoquinone in mice causes a painful spasm, which can be reduced with antispasmodic substances (causal medication) and analgesic substances (symptomatic medication).

The test was carried out on batches of 10 male mice, of the Swiss strain, having an average weight of 22 g±2. The spasmodic and painful syndrome caused by the intraperitoneal injection of 0.25 ml of the phenylbenzoquinone solution is characterized by hind limb stretching movements and dorsoabdominal musculature twisting movements, which accounted for a period of time of 30 min, starting from 15 min following the administration of the phenylbenzoquinone.

An antispasmodic and analgesic effect manifests itself through a reduction in the number of spasmodic attacks, which is dependent on the dose. For each test, the substance being studied is administered by means of an esophageal tube, 30 min before the phenylbenzoquinone.

For experimental ease, the following were used:
phloroglucinol Lyoc (lyophilizate), and
effervescent paracetamol (tablet);
the two substances being perfectly soluble and miscible.

To test the products administered in isolation (prior art), on the one hand, phloroglucinol lyocs (lyophilized systems) were dissolved in distilled water, and on the other hand, effervescent paracetamol tablets were solubilized in distilled water (the solution obtained has a pH of 5).

To test the pharmaceutical compositions of the invention, such phloroglucinol lyocs (lyophilized systems) and such effervescent paracetamol tablets were dissolved and solubilized together. The solution which contains the two active ingredients itself also has a pH of 5.

Given the metabolism in this animal species, the mouse, which is more accelerated than in humans, those skilled in the art, specialists in pharmacology, most commonly use doses which are multiples of the human dose in order to be able to readily objectivize the results.

The results are expressed as percentage of inhibition of the spasm and of the pain relative to control animals which receive only 20 ml/kg of distilled water.

Said results are recorded in the table below, accompanied by the statistical calculation.

TABLE

| | | % inhibition | Statistics |
|---|---|---|---|
| Phloroglucinol | 40 mg/kg | 7 | |
| Paracetamol | 50 mg/kg | 37 | * |
| Combination | | 65 | *** |
| Phloroglucinol | 80 mg/kg | 21 | |
| Paracetamol | 50 mg/kg | 39 | * |

TABLE-continued

| | | % inhibition | Statistics |
|---|---|---|---|
| Combination | | 85 | *** |
| Phloroglucinol | 100 mg/kg | 27 | * |
| Paracetamol | 50 mg/kg | 40 | ** |
| Combination | | 95 | *** |
| Phloroglucinol | 120 mg/kg | 32 | * |
| Paracetamol | 50 mg/kg | 39 | ** |
| Combination | | 100 | *** no contraction |

* $p = 0.05$
** $p = 0.01$
*** $p = 0.001$

The examination of these results shows that, whatever the doses used, a potentiating synergy (from 40% to 50%) of the phloroglucinol+paracetamol combination, on the painful spasm, is always demonstrated. This synergy is already highly statistically significant from the low doses onward ($p=0.001$), and it always increases with the increase in doses.

It is noted that, for a combination of 120 mg of phloroglucinol and 50 mg of paracetamol (per kg), there is no contraction. The animals are completely protected (saturated system).

The above numbers most certainly demonstrate the unobvious nature of the invention and also the great advantage thereof.

The invention claimed is:

1. A pharmaceutical composition for oral or rectal administration, comprising phloroglucinol, paracetamol, and a pharmaceutically acceptable excipient, wherein the pharmaceutical composition is in a form selected from the group consisting of tablets, capsules, powders, granules, lyophilizates, syrups, suspensions, and suppositories.

2. The pharmaceutical composition as claimed in claim 1 wherein the composition is in the form of an effervescent tablet.

3. The pharmaceutical composition as claims in claim 2, wherein the effervescent tablet further comprises
   at least one organic acid and/or at least one salt of an organic acid, said organic acid being selected from the group consisting of citric acid, tartaric acid, malic acid and acetic acid, and
   at least one strong base and/or at least one salt of a strong base, said at least one salt of a strong base being selected from the group consisting of sodium bicarbonate, sodium carbonate, calcium bicarbonate, calcium carbonate, magnesium bicarbonate, magnesium carbonate, potassium bicarbonate and potassium carbonate.

4. The pharmaceutical composition as claims in claim 1, wherein the phloroglucinol is present at a dose of between 50 and 200 mg.

5. The pharmaceutical composition as claimed in claim 1, wherein the paracetamol is present at a dose of between 100 and 1000 mg.

6. The pharmaceutical composition of claim 4, wherein the phloroglucinol is present at a dose of 80, 100 or 160 mg.

7. The pharmaceutical composition of claim 4, wherein the paracetamol is present at a dose of between 100 and 500 mg.

8. A method of treating a spasmodic condition in a patient comprising orally or rectally administering to the patient a therapeutically effective amount of a pharmaceutical composition according to claim 1.

9. The method of claim 8, wherein the spasmodic condition is spastic colitis, hepatic colic, nephritic colic, or dysmenorrheal.

10. The pharmaceutical composition as claimed in claim 1, wherein the composition is in a form selected from the group consisting of tablets, capsules, powders, granules, lyophilizates, and suppositories.

11. The pharmaceutical composition as claimed in claim 1, wherein the composition is in a solid form.

12. A pharmaceutical composition comprising phloroglucinol, paracetamol, and a pharmaceutically acceptable excipient, the composition formulated for oral or rectal administration.

13. The pharmaceutical composition according to claim 12, wherein the composition is in a form selected from the group consisting of tablets, capsules, powders, granules, lyophilizates, syrups, suspensions, and suppositories.

* * * * *